(12) United States Patent
Wang

(10) Patent No.: US 6,423,351 B2
(45) Date of Patent: Jul. 23, 2002

(54) INHIBITING OXIDATIVE DEGRADATION OF PHARMACEUTICAL FORMULATIONS

(75) Inventor: Hai Wang, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/803,455

(22) Filed: Mar. 9, 2001

Related U.S. Application Data

(60) Provisional application No. 60/188,447, filed on Mar. 10, 2000.

(51) Int. Cl.$^7$ .................. A61K 33/26; A61K 47/02; A61K 31/295; A61K 31/40; A61K 31/439

(52) U.S. Cl. .................. 424/648; 514/299; 514/305; 514/424; 514/428; 514/502; 514/579; 514/769; 514/970; 424/DIG. 6

(58) Field of Search .................. 514/299, 305, 514/424, 428, 502, 579, 769, 970; 424/648, DIG. 6

(56) References Cited

U.S. PATENT DOCUMENTS

| 4,083,951 A | | 4/1978 | Goudie et al. ............. 424/44 |
| 5,817,047 A | * | 10/1998 | Osborn, III et al. .......... 604/14 |
| 6,013,632 A | * | 1/2000 | Jones et al. .................. 514/17 |

FOREIGN PATENT DOCUMENTS

WO WO9830228 7/1998

OTHER PUBLICATIONS

Chemical Abstracts 112:97240, 1990.*
H. van Doorne, et al., Pharmacy World & Science, vol. 16, No. 1, 1994, "The Preservation of Some Oral Liquid Preparations".

* cited by examiner

*Primary Examiner*—John Pak
(74) *Attorney, Agent, or Firm*—Peter C. Richardson; Gregg C. Benson; Carl J. Goddard

(57) ABSTRACT

The invention provides methods for inhibiting oxidative degradation of pharmaceutical formulations comprising at least one oxidation-susceptible active drug ingredient which methods comprise adding an oxidation-inhibiting amount of a ferrous ion source, preferably in the form of a pharmaceuticalexcipient, to the formulation.

The invention further provides pharmaceutical formulations comprising at least one oxidation-susceptible active drug ingredient and an oxidation-inhibiting amount of a ferrous iron source, preferably in the form of a pharmaceuticalexcipient.

The invention still further provides for the use of a ferrous ion source as an anti-oxidant in pharmaceutical formulations.

7 Claims, No Drawings

INHIBITING OXIDATIVE DEGRADATION OF PHARMACEUTICAL FORMULATIONS

CROSS REFERENCE TO RELATED APPLICATION

This application claims the benefit of U.S. Provisional Application No. 60/188,447 filed Mar. 10, 2000.

BACKGROUND OF THE INVENTION

The invention relates to methods of inhibiting oxidative degradation of pharmaceutical formulations comprising at least one oxidation-susceptible active drug ingredient and to pharmaceutical formulations comprising oxidation-inhibiting excipients.

The desirability of providing pharmaceutical formulations in which an oxidation-susceptible active drug ingredient or ingredients are protected against oxidative degradation inherent to prolonged storage is a concept well known to, and appreciated by, one of ordinary skill in the art. Antioxidants commonly employed in various pharmaceutical formulations may include, inter alia, vitamin E, ascorbic acid, BHT (butylated hydroxytoluene), BHA (butylated hydroxyanisole), and the like.

Pharmaceutical formulations comprising ferrous ion sources as nutritional supplements are generally well known in the art. The presence of ferrous ion sources in pharmaceutical formulations has additional utility in other capacities. For example, it has been reported that preservation of oral liquid preparations from bacterial contamination can be achieved by treatment with, inter alia, certain ferrous sulfate/methylparaben mixtures. See H. van Doorne, et al., Pharmacy World & Science, 16 (1), 18–21 (1994). It has also been reported that the addition of ferrous salts to compositions comprising acetylsalicylic acid, or salts thereof, reduces the propensity of the compositions to induce gastric irritation. See A. Goudie, et al., U.S. Pat. No. 4,083,951.

The present invention discloses methods for protecting an oxidation-susceptible active drug ingredient or ingredients in a pharmaceutical formulation from oxidative degradation which methods comprise adding a ferrous ion source to the formulation, preferably in the form of a pharmaceutical excipient comprising the formulation components. In this manner, pharmaceutical formulations are produced in which the active drug ingredient or ingredients are protected from oxidative degradation, thus facilitating storage of the formulation over extended periods of time.

SUMMARY OF THE INVENTION

The instant invention provides methods for inhibiting oxidative degradation of pharmaceutical formulations comprising at least one oxidation-susceptible active drug ingredient which comprises protecting the formulation by the addition of an oxidation-inhibiting amount of a ferrous ion source thereto, preferably in the form of a pharmaceutical excipient.

The invention further provides pharmaceutical formulations comprising at least one oxidation-susceptible active drug ingredient and an oxidation-inhibiting amount of a ferrous iron source, preferably in the form of a pharmaceuticalexcipient.

The invention still further provides for the use of a ferrous ion source as an anti-oxidant in pharmaceutical formulations.

DETAILED DESCRIPTION OF THE INVENTION

The instant invention provides methods of inhibiting oxidative degradation of pharmaceutical formulations comprising at least one oxidation-susceptible active drug ingredient which methods comprise adding to the formulation an oxidation-inhibiting amount of a ferrous ion source, preferably in the form of a pharmaceuticalexcipient.

The invention further provides pharmaceutical formulations comprising at least one oxidation-susceptible active drug ingredient and an oxidation-inhibiting amount of a ferrous iron source, preferably in the form of a pharmaceuticalexcipient.

The invention still further provides for the use of a ferrous ion source as an anti-oxidant in pharmaceutical formulations.

As employed throughout the instant description and appendant claims, the term "ferrous" denotes a salt comprising the element iron in its lowest valence state, i.e. $Fe^{+2}$.

According to the methods of the invention, a formulation comprising at least one oxidation-susceptible active drug ingredient is protected against oxidative degradation by the addition of an oxidation-inhibiting amount of a ferrous ion source thereto. Although a broad spectrum of pharmaceutical formulations comprising at least one oxidation-susceptible active drug ingredient will benefit from the augmented protection to oxidative degradation provided by the methods of the instant invention, formulations comprising an active ingredient or ingredients incorporating at least one amine or benzyl functional group are particularly benefited. Preferably, the ferrous ion source should be, for purposes of penultimate formulation, substantially soluble in water or a lower molecular weight alcohol, for example, methanol, ethanol, or isopropanol, and should also be chemically compatible with the active drug ingredient or ingredients and any additional components comprising the formulation. The ferrous ion source comprising the formulation should also be toxicologically compatible with the subject being treated. Accordingly, ferrous ion sources that are unstable, chemically incompatible with the active ingredient or ingredients comprising the formulation, or toxicologically incompatible with the subject being treated, are not preferred. Generally preferred ferrous ion sources may comprise, for example, ferrous sulfate, ammonium ferrous sulfate, ferrous chloride, ferrousgluconate, ferrous citrate, ferrous fumarate, ferrous lactate, ferrous carbonate, chelated and hydrated forms thereof, and mixtures thereof. Particularly preferred ferrous ion sources comprise those compounds selected from the group consisting of ferrous sulfate, ammonium ferrous sulfate hexahydrate, and ferrous chloride. Ammonium ferrous sulfate hexahydrate is especially preferred.

Although the ferrous ion source and the active drug ingredient or ingredients comprising the formulation may be compounded by simple intimate admixture, it is generally preferred that the ferrous ion source comprise at least a portion of a pharmaceutical excipient. Such excipients are well known to one of ordinary skill in the art and may comprise, for example, dicalcium phosphate, sodium citrate, calcium carbonate, microcrystalline cellulose, silicified microcrystalline cellulose, lactose, kaolin, mannitol, starch, sucrose, dextrose, and the like. The excipient comprising the ferrous ion source may be prepared by conventional methods well known to one of ordinary skill in the art. For example, the excipient may be prepared by spraying or intimately admixing a solution of the ferrous ion source at an appropriate or desired concentration with the other components comprising the excipient. Once the excipient comprising the ferrous ion source has been uniformly admixed, for example, by mixing in a high shear mixer, it is dried thoroughly, for example, in a fluid bed dryer or an oven dryer. Preferably, the dried excipient is then passed through a mill or screen to ensure that a uniform particle size has been achieved. Although the concentration of the ferrous ion source may vary, it typically comprises from about 0.001% to about 5.0% by weight of the formulation. Preferably, the concentration of the ferrous ion source comprises from about 0.002% to about 0.02% by weight, based upon the amount of the excipient present in the formulation. For example, if a fomulation contained 100 g of excipients, it would preferably contain about 1 mg to about 5 g of ferrous ion source. An amount comprising about 0.01% by weight of the formulation is especially preferred. These amount ranges may, of course, be varied somewhat according to the active drug ingredient or ingredients to be stabilized as will be recognized and appreciated by one of ordinary skill in the art having benefit of the teachings of the instant disclosure. The ability to select an appropriate ferrous ion source as well as an effective amount thereof to protect a particular pharmaceutical formulation comprising at least one oxidation-susceptible active drug ingredient against oxidative degradation according to the methods of this invention is within the purview of one of ordinary skill in the art having the benefit of the instant disclosure.

Generally, methods of preparing solid dosage formulations comprising an active ingredient or ingredients and a pharmaceutical excipient are well known, or will be readily apparent in light of the instant disclosure, to of one of ordinary skill in the art. See, for example, Remington's Pharmaceutical Sciences, Mack Publishing Company, Easton, Pa., 18th Edition (1990). The pharmaceutical formulations of this invention may comprise any conventional solid dosage form including, for example, tablets, pills, capsules, and the like. The formulations may further comprise a binder such as hydroxypropylmethyl cellulose, gum tragacanth, acacia gum, corn starch or gelatin; a disintegrating agent such as corn starch, potato starch,alginic acid, sodium starch gylcolate, croscamellose sodium, or crospovidone; a lubricant such as magnesium stearate; and a sweetening agent such as sucrose, lactose, or saccharin. Various other materials may be present in the form of coatings or to modify the physical form of the dosage unit. For instance, tablets may be coated with mixtures comprising, for example, titanium dioxide, dextrose, polyethylene glycol, sodium carboxymethyl cellulose, dextrin, and the like. The coatings may also comprise the form of an enteric polymer including phthalate derivatives, such as cellulose acetate phthalate, polyvinylacetate phthalate and hydroxypropylmethyl cellulose phthalate, polyacrylic acid derivatives, such as methacrylic acid copolymer, vinyl acetate, and crotonic acid copolymers.

It is to be understood that the examples of the invention set forth hereinbelow are not to be construed as limitations thereof, as additional embodiments within the scope of the appendant claims will be known, or apparent in light of the instant disclosure, to one of ordinary skill in the art.

EXPERIMENTAL

The compound (2S,3S)-N-(5-isopropyl-2-methoxyphenyl)methyl-2-diphenylmethyl-1-azabicyclo[2.2.2]octan-3-amine, to be referred to hereinafter as Compound 1, prepared as described in U.S. Pat. No. 5,807,867; and the tartrate salt of the compound cis-6-phenyl-5-[4-(2-pyrrolidin-1-yl-ethoxy)-phenyl]-5,6,7,8-tetrahydronaphthalen-2-ol (lasofoxifene tartrate), to be referred to hereinafter as Compound 2, prepared as described in U.S. Pat. No. 5,552,412. were formulated into solid dosage formulations as described hereinbelow.

Compound 1 was formulated with, inter alia, excipients comprising about 0.01% by weight of ammonium ferrous sulfate hexahydrate into solid binary pharmaceutical formulations as follows. A solution of 350 mg of ferrous ammonium sulfate hexahydrate, dissolved in 100 ml of pure water, was added to 500 g of microcrystalline cellulose (Avicel®; FMC; Philadelphia, Pa.) and the mixture was mixed thoroughly for about ten minutes. The mixture was then dried in an Aeromatic fluid-bed dryer (Niro Inc.; Columbia, Md.) at an inlet temperature of 65° C. The dried Avicel® excipient so prepared comprising the ferrous ion source was milled through a Mini-Comil 193 (Quadro Engineering; Waterloo, Ontario, Canada) with a stainless steel screen. This identical procedure was employed to prepare excipients comprising lactose and the ferrous ion source. A pre-determined amount of Compound 1, the dried Avicel® or lactose excipient comprising the ferrous ion source, and crospovidone (BASF Corp.; Mount Olive, N.J.) were added to a stainless steel V-blender and blended for about 20 minutes. Magnesium stearate was then added and the resulting mixture was blended for an additional five minutes. The lubricated granulate so prepared was roll-compacted on a TF-min Roller Compactor (Vector Corporation; Marion, Iowa) utilizing a roller speed of six rpm, a screw-feeder speed of 16 rpm, and a roller pressure of 20 kg/cm$^2$. The compacted ribbons so produced were milled with a rotary granulator with a 20 mesh stainless steel screen. The granulate so produced was transferred into a four quarter V-blender and blended for five minutes. The second half portion of magnesium stearate was then added and blended for an additional five minutes. The lubricated granulate so produced was compressed on a rotary-type Kilian T-100 tablet press (Kilian & Co.; Horsham, Pa.). Tablets were compressed at a weight of about 300 mg for 100 mg potency formulations using a standard round concave ⅜" punch.

The tablets so prepared were stored under accelerated stability conditions, i.e. at 40° C. at 75% relative humidity and 50° C. at 20% relative humidity for six weeks. Reversed-phase ion pair liquid chromatography (RPLC) was then employed to separate Compound I from its isopropyloxide (M+16) and isopropylperoxide (M+32) oxidative degradation products. RPLC was performed utilizing a Waters Symmetry C$_8$ column (Waters Instrument Co.; Milford, Mass.) 15 cm length×3.9 mm I.D. at a temperature of 40° C. using a mobile phase of 0.1 M C$_8$H$_{17}$O$_3$SNa in 0.05 M KH$_2$PO$_4$ (pH 3.0): acetonitrile (55:45 v/v), a flow rate of 1.0 mL/min., and an injection volume of 20 μL at a run time of 60 minutes.

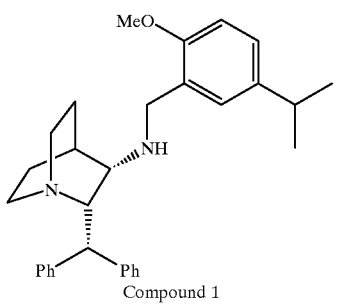

Compound 1

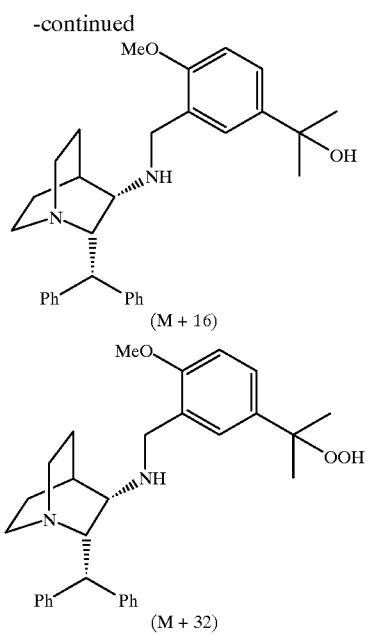

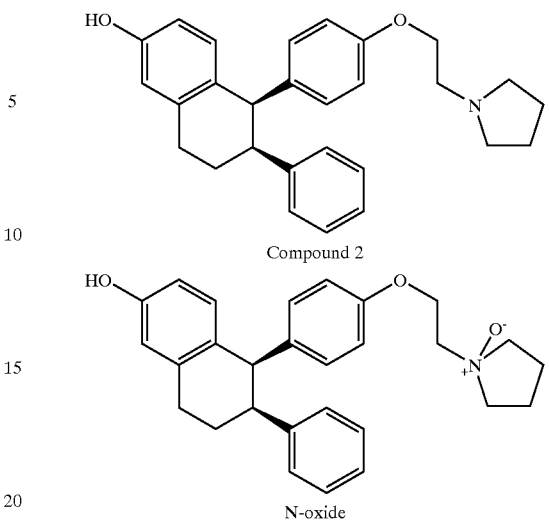

As summarized hereinbelow in Tables 1 and 2, the formation of the isopropyloxide (M+16) and isopropylperoxide (M+32) oxidative degradation by-products of Compound 1 was inhibited significantly by the addition of the ferrous ion source to the formulation.

As indicated in Table 1, formation of the M+16 and M+32 oxidative degradation by-products of Compound 1 was reduced from 0.22% and 0.41%, in the samples comprising only Compound 1 and Avicel®, to 0.07% and 0.04%, respectively, in the samples comprising Compound 1, Avicel®, and 0.01% of ferrous ion.

Similarly, as indicated in Table 2, formation of the M+16 and M+32 oxidative degradation by-products of Compound 1 was reduced from 0.16% and 0.27%, in the samples comprising only Compound 1 and lactose, to 0.06% and 0.00%, respectively, in the samples comprising Compound 1, lactose, and 0.01% of ferrous ion.

Compound 2 was similarly formulated with, inter alia, excipients comprising about 0.01% of ferrous ammonium sulfate hexahydrate into solid binary pharmaceutical formulations. The excipients further included microcrystalline cellulose (Avicel®), lactose, or silicified microcrystalline cellulose (Prosolv®; Penwest Pharmaceuticals; Patterson, N.Y.).

The formulations so prepared were then stored under accelerated stability conditions, i.e. at 40° C. at 75% relative humidity and 50° C. at 20% relative humidity for six weeks. Reversed-phase ion pair liquid chromatography (RPLC) was used to separate Compound 2 from its N-oxide oxidative degradation product. RPLC was performed utilizing a Waters Symmetry $C_{18}$ column (Waters Instrument Co.; Milford, Mass.) 15 cm length×3.9 mm I.D. at a temperature of 40° C. using a mobile phase of buffer (20 mM $KH_2PO_4$ (pH adjusted to 3.0 with phosphoric acid, with 0.1% octanesulfonic acid): acetonitrile (60:40 v/v), a flow rate of 1.0 mL/min., and an injection volume of 10 μL at a run time of 35 minutes.

As summarized hereinbelow in Table 3, the formation of the N-oxide oxidative degradation by-product of Compound 2 was inhibited significantly by the addition of the ferrous ion source to the formulations. For example, formation of the N-oxide oxidative degradation by-product of Compound 2 was reduced from 5.07%, in the formulation comprising only Compound 2 and lactose, to 0.07% in the formulation comprising Compound 2, lactose and 0.01% of ferrous ion. Similarly, formation of the N-oxide oxidative degradation by-product of Compound 2 was reduced from 5.50%, in the formulation comprising only Compound 2 and Avicel®, to 0.70% in the formulation comprising Compound 2, Avicel® and 0.01% of ferrous ion. Finally, formation of the N-oxide oxidative degradation by-product of Compound 2 was reduced from 3.30%, in the formulation comprising only Compound 2 and Prosolv®, to 0.30% in the formulation comprising Compound 2, Prosolv® and 0.01% of ferrous ion.

TABLE 1

Stability Results of Binary Mixture of Avicel ® and Compound 1

| | % M + 16 by-product by RPLC | % M + 32 by-product by RPLC |
|---|---|---|
| Compound 1 and Avicel ® | 0.22% | 0.41% |
| Compound 1, Avicel ® and 0.01% $Fe^{+2}$ | 0.07% | 0.04% |

TABLE 2

Stability Results of Binary Mixture of Lactose and Compound 1

| | % M + 16 by-product by RPLC | % M + 32 by-product by RPLC |
|---|---|---|
| Compound 1 and lactose | 0.16% | 0.27% |
| Compound 1, lactose and 0.01% $Fe^{+2}$ | 0.06% | 0.00% |

TABLE 3

Stability Results of Binary Mixture of Lactose, Avicel ®, or Prosolv ®
With Compound 2

| | % Compound 2 N-Oxide by RPLC |
|---|---|
| Compound 2 and lactose | 5.07% |
| Compound 2, lactose and 0.01% $Fe^{+2}$ | 0.07% |
| Compound 2 and Avicel ® | 5.50% |
| Compound 2, Avicel ® and 0.01% $Fe^{+2}$ | 0.70% |
| Compound 2 and Prosolv ® | 3.30% |
| Compound 2, Prosolv ® and 0.01% $Fe^{+2}$ | 0.30% |

What is claimed is:

1. A method of inhibiting oxidative degradation of a pharmaceutical formulation comprising at least one oxidation-susceptible active drug ingredient having at least one amine or benzyl functional group which method comprises adding to said formulation an oxidative degradation-inhibiting amount of a ferrous ion source.

2. A method according to claim 1 wherein said ferrous ion source comprises ferrous sulfate, ammonium ferrous sulfate, ferrous gluconate, ferrous citrate, ferrous fumarate, ferrous lactate, ferrous carbonate, and ferrous chloride, chelated and hydrated forms thereof, and mixtures thereof.

3. A method according to claim 2 wherein said ferrous ion source is selected from the group consisting of ferrous sulfate, ammonium ferrous sulfate hexahydrate, and ferrous chloride.

4. A method according to claim 1 wherein said ferrous ion source comprises at least a portion of a pharmaceutical excipient.

5. A method according to claim 1 wherein said ferrous ion source comprises from about 0.001 % to about 5.0 % by weight of said formulation.

6. A method according to claim 5 wherein said ferrous ion source comprises from about 0.002 % to about 0.02 % by weight of said formulation.

7. A method according to claim 6 wherein said ferrous ion source comprises about 0.01 % by weight of said formulation.

* * * * *